(12) United States Patent
Sotoyama

(10) Patent No.: US 7,571,894 B2
(45) Date of Patent: Aug. 11, 2009

(54) ORGANIC ELECTROLUMINESCENCE ELEMENT

(75) Inventor: Wataru Sotoyama, Kawasaki (JP)

(73) Assignee: Fuji Photo Film Co., Ltd., Minami-Ashigara-shi (JP)

( * ) Notice: Subject to any disclaimer, the term of this patent is extended or adjusted under 35 U.S.C. 154(b) by 276 days.

(21) Appl. No.: 11/074,899

(22) Filed: Mar. 9, 2005

(65) Prior Publication Data
US 2005/0156164 A1 Jul. 21, 2005

Related U.S. Application Data

(63) Continuation of application No. PCT/JP03/05417, filed on Apr. 28, 2003.

(51) Int. Cl.
*C07C 211/43* (2006.01)
*H01L 51/54* (2006.01)

(52) U.S. Cl. .................. 254/40; 257/E51.049; 564/308

(58) Field of Classification Search .................. 257/40, 257/E51.049, E51.05; 438/82, 99; 546/26, 546/38; 562/470–471; 564/307–308
See application file for complete search history.

(56) References Cited

U.S. PATENT DOCUMENTS

| | | | | |
|---|---|---|---|---|
| 6,818,324 | B1 * | 11/2004 | Utsugi et al. | 428/690 |
| 7,060,370 | B2 * | 6/2006 | Kinoshita et al. | 428/690 |
| 7,128,982 | B2 * | 10/2006 | Oshiyama et al. | 428/690 |
| 7,233,019 | B2 * | 6/2007 | Ionkin et al. | 257/40 |
| 2002/0038860 | A1 * | 4/2002 | Tsuboyama et al. | 252/301.16 |
| 2004/0081854 | A1 * | 4/2004 | Hirose et al. | 428/690 |
| 2005/0238910 | A1 * | 10/2005 | Ionkin et al. | 428/690 |

FOREIGN PATENT DOCUMENTS

| | | |
|---|---|---|
| EP | 0 926 216 A1 | 6/1999 |
| JP | 2001-118682 | 4/2001 |
| JP | 2002-63988 | 2/2002 |
| JP | 2002-124385 | 4/2002 |

OTHER PUBLICATIONS

Machine Translation of Patent Abstracts of Japan document 2001-118682.*
C. W. Tang et al.; "Organic electroluminescent diodes", Appl. Phys. Lett. 51 (12); Sep. 21, 1987. pp. 913-915.
C. W. Tang et al.; "Electroluminescence of doped organic thin films", J. Appl. Phys. 85 (9); May 1, 1989, pp. 3610-3616.
Matthias Beinhoff et al., "Towards Dendrimers with Solvent-Induced and Quantifyable Polarity Gradient", Polymeric Materials Science and Engineering, 2001, 84, pp. 751-752, XP008065060.
European Search Report, dated Jun. 20, 2006, issued in corresponding European Application No. 03 72 8002.

* cited by examiner

*Primary Examiner*—Douglas M Menz
*Assistant Examiner*—Matthew W Such
(74) *Attorney, Agent, or Firm*—Westerman, Hattori, Daniels & Adrian, LLP.

(57) ABSTRACT

This organic electroluminescence element has an organic light-emitting layer between a positive electrode and a negative electrode, wherein the organic light-emitting layer contains a 1,3,6,8-tetrasubstituted pyrene compound having a specific structure as an organic light-emitting layer forming material. Provided are an organic light-emitting layer forming material that emits blue light with a high color purity, has a high luminous efficiency, and is stable for a long duration of operation, when used singly or as a guest, an organic EL element having a high luminous efficiency and a long operation lifetime, and a high-performance organic EL display that has a high luminous efficiency and a long operation lifetime.

16 Claims, 2 Drawing Sheets

ORGANIC ELECTROLUMINESCENCE ELEMENT

CROSS REFERENCE TO RELATED APPLICATIONS

This application is a continuation of international application PCT/JP2003/005417, filed on Apr. 28, 2003.

BACKGROUND OF THE INVENTION

1. Field of the Invention

The present invention relates to an organic light-emitting layer forming materials for an organic electroluminescence element (also called an organic EL element, hereinafter), an organic EL element, and organic EL display.

2. Description of the Related Art

Since a layer-type element in which a positive hole transporting organic thin film and electron transporting organic thin film were layered, was reported (C. W. Tang and S. A. VanSlyke, Applied Physics Letters, vol. 51, p. 913, 1987, for example), organic EL elements have been expected to be applied to flat panel displays as display elements having features such as self emission and high-speed response. They are a focus of particular interest as large-area light-emitting elements that emit light at a low voltage of not more than 10 V.

Fundamentally, a layered-type organic EL element has a structure of a positive electrode/positive hole transporting layer/organic light-emitting layer/electron transporting layer/negative electrode. Of these, the positive hole transporting layer or electron transporting layer can also play the role of an organic light-emitting layer, as in the case of the above-described two-layer type element of Tang and VanSlyke.

In order to obtain an organic EL element having a high luminous efficiency (that is, light emitting efficiency), it is necessary for the organic light-emitting layer to have a high luminous efficiency. For the constitution of the organic light-emitting layer, a pigment-doped film to which a small quantity of pigment molecules that emit strong fluorescence are doped as a guest into the major component in the capacity of a host material has been proposed, besides a single film formed from a single kind of material (for example, C. W. Tang, S. A. VanSlyke and C. H. Chen, Journal of Applied Physics, vol. 65, p. 3610, 1989).

However, the need for materials that have high luminous efficiency and are stable in a long duration of operation is not fully met by the present organic light-emitting layer forming materials for use in such applications.

As organic light-emitting layer forming materials, those having a polycyclic aromatic ring in the light-emitting molecular structure (for example, Japanese Unexamined Patent Application Publication No. 2002-124385 (claims)), and 1,3,6,8-tetraphenylpyrene derivatives (for example, Japanese Unexamined Patent Application Publication No. 2001-118682 (claims).) are known.

SUMMARY OF THE INVENTION

Accordingly, it is an object of the present invention to solve the above-described problems, and provide an organic EL element having a high luminous efficiency and a long operation lifetime, a high-performance organic EL display using the element, and an organic light-emitting layer forming material therefor that emits blue light with a high color purity, has a high luminous efficiency, and is stable for a long duration of operation, when used singly or as a guest. The other objects and advantages of the present invention will be explained in the following explanation.

According to one aspect of the present invention, provided is a 1,3,6,8-tetrasubstituted pyrene compound represented by the following formula (1),

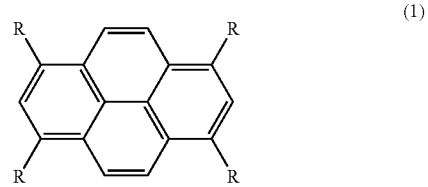

(in formula (1), R's have, independently from each other, a structure represented by the following formula (2),

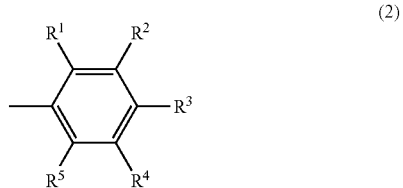

(in formula (2), $R^1$-$R^5$ are, independently from each other, hydrogen or a substituent group; and at least one of $R^1$-$R^5$ is either one of the groups represented by the following formulae (3)-(6)),

(in formulae (3) to (6), $R^6$-$R^{12}$ are, independently from each other, hydrogen or a substituent group.)

Preferable are that $R^6$ and $R^7$ in formula (3) are, independently from each other, an aromatic group that may have a substituent group; that $R^{12}$ in formula (6) is an aromatic group that may have a substituent group; that the compound is used as an organic light-emitting layer forming material in an organic electroluminescence element, or as an organic light-emitting layer forming material in the capacity of a host or a guest in an organic electroluminescence element, in particular; and other similar embodiments.

By the present invention, an organic light-emitting layer forming material that emits blue light with a high color purity, has a high luminous efficiency, and is stable for a long duration of operation, when used singly or as a guest, is provided.

According to another aspect of the present invention, provided is an organic electroluminescence element containing the above-described 1,3,6,8-tetrasubstituted pyrene compound as an organic light-emitting layer forming material.

It may be preferable that the 1,3,6,8-tetrasubstituted pyrene compound represented by formula (1) is an organic light-emitting layer forming material in the capacity of a host or a guest; or that the organic light-emitting layer is a single layer of a 1,3,6,8-tetrasubstituted pyrene compound represented by formula (1).

Preferable are that the organic light-emitting layer contains one or more aromatic amine compounds represented by the following formula (7),

(7)

(in formula (7), $Ar^1$ is a di, tri or tetravalent aromatic group that may have a substituent group; $R^{17}$ and $R^{18}$ are, independently from each other, a monovalent aromatic group that may have a substituent group; and n is an integer of 2-4.);

particularly that the aromatic amine compound represented by formula (7) is N,N'-dinaphthyl-N,N'-diphenyl-[1,1'-biphenyl]-4,4'-diamine represented by the following formula (8);

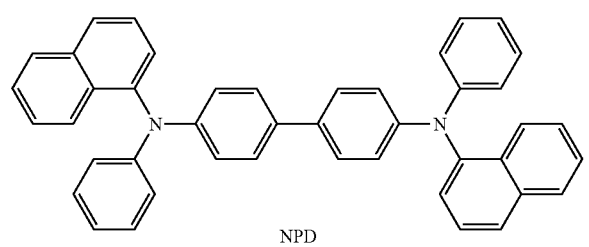
(8)

NPD that the organic light-emitting layer contains one of more carbazole compounds represented by the following formula (9),

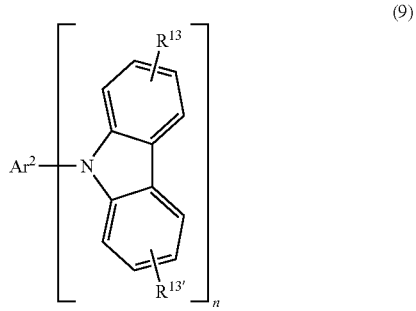
(9)

(in formula (9), $Ar^2$ is a di, tri or tetravalent aromatic group that may have a substituent group; $R^{13}$ and $R^{13'}$ are, independently from each other, a hydrogen atom, a halogen atom, or an alkyl, aralkyl, alkenyl, aromatic, cyano, amino, acyl, alkoxycarbonyl, carboxy, alkoxy, alkylsulfonyl, hydroxyl, amide or aromatic oxy group that may have a substituent group; and n is an integer of 2-4.); particularly that the carbazole compound represented by formula (9) is 4,4'-bis(9-carbazolyl)-biphenyl represented by the following formula (10);

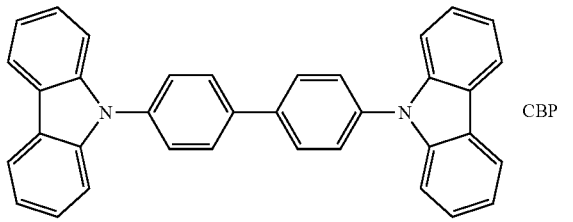
(10)

CBP that the organic light-emitting layer contains one or more hydroxyquinoline-oxyaryl complex represented by the following formula (11),

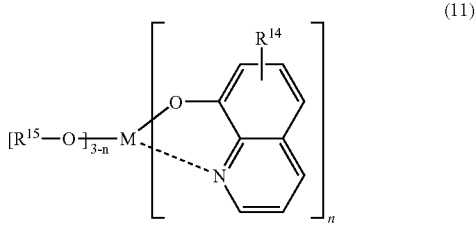
(11)

(in formula (11), $R^{14}$ is hydrogen or an alkyl group that may have a substituent group; $R^{15}$ is an aromatic group that may have a substituent group; M is a trivalent metal; and n is 1 or 2.);

and particularly that the hydroxyquinoline-oxyaryl complex represented by formula (11) is an aluminum hydroxyquinoline-oxybiphenyl complex represented by the following formula (12).

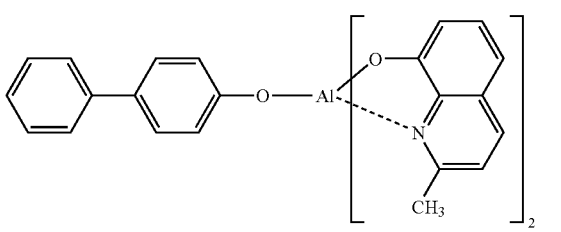
(12)

According to this aspect of the present invention, an organic EL element having a high luminous efficiency and a long operation lifetime is provided.

According to still another aspect of the present invention, provided is an organic EL display using the above-described organic EL element.

According to this aspect of the present invention, a high-performance organic EL display using an organic EL element having a high luminous efficiency and a long operation lifetime is provided.

DESCRIPTION OF THE PREFERRED EMBODIMENTS

Figure 1:
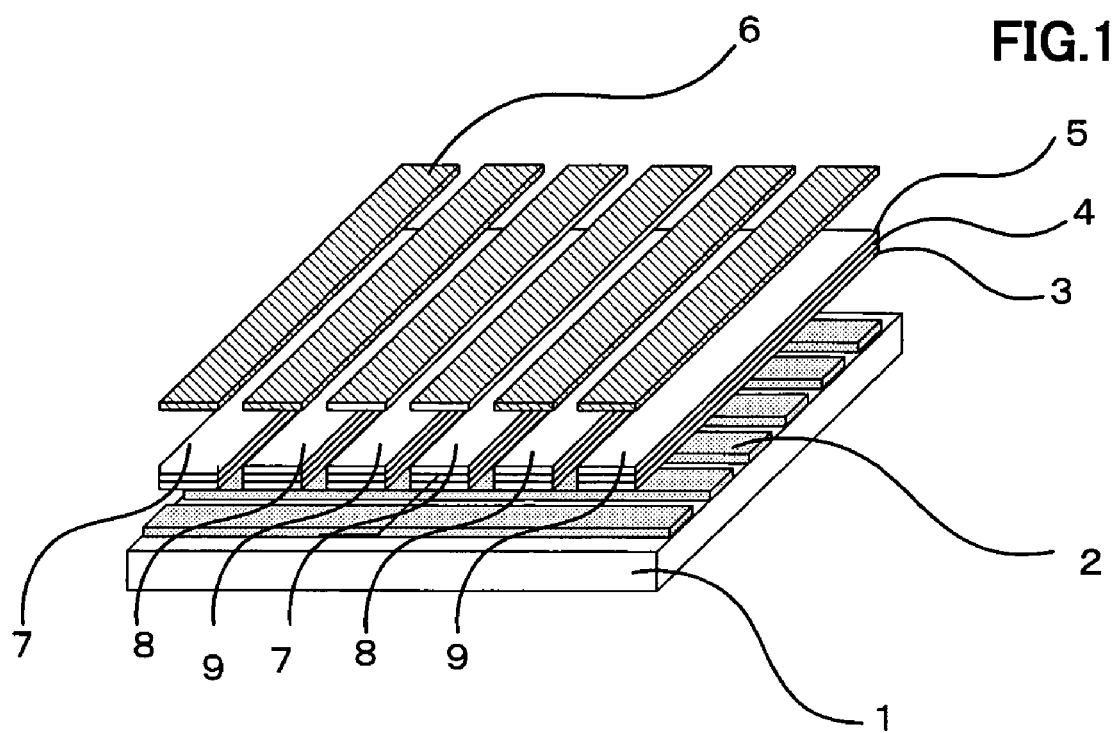
FIG. 1 is a schematic perspective view showing an organic EL element according to the present invention that is used in a passive matrix display.

The embodiments of the present invention are described hereinafter referring to the drawings, formulae, examples, etc. However, such drawings, formulae, examples, etc. plus the explanation are for the sake of exemplifying the present invention, and not intending to limit the scope of the invention. It goes without saying that other embodiments should also be included in the category of the present invention as far as they conform to the gist of the present invention. In the drawings, the same numerals refer to the same elements.

As a result of the investigations on the above-described problems, it was found that an organic EL element formed using a particular 1,3,6,8-tetrasubstituted pyrene compound as an organic light-emitting layer forming material, emits light with a high luminous efficiency, has a long operation lifetime, and enables stable operation. Such a 1,3,6,8-tetrasubstituted pyrene compound can be obtained by relatively easy synthetic processes.

As one of the means to apply an organic EL element to full color display, a method is widely employed in which red, green and blue organic EL elements are prepared, and one pixel is formed by combining these three elements. A high color purity is required for each color emitted from organic EL elements for use in such full color display. The organic EL element according to the present invention emits blue light with a high color purity, when the organic light-emitting layer forming material according to the present invention is used singly or as a guest.

The chemical structure of a specific 1,3,6,8-tetrasubstituted pyrene compound that is an organic light-emitting layer forming material according to the present invention can be represented by formula (1).

In formula (1), R's have, independently from each other, a structure represented by formula (2). In formula (2), $R^1$-$R^5$ are, independently from each other, hydrogen or a substituent group, and at least one of $R^1$-$R^5$ is either one of the groups represented by formulae (3)-(6).

In formulae (3) to (6), $R^6$-$R^{12}$ are, independently from each other, hydrogen or a substituent group.

As examples of $R^1$-$R^{12}$, enumerated are hydrogen, a straight-chain or branched-chain aliphatic group that may have a substituent group, an aromatic group that may have a substituent group, and an alicyclic group that may have a substituent group. In any case, elements other than carbon and hydrogen, such as oxygen, sulfur, nitrogen or the like may be included in the structure. It is to be noted that in the present invention including the following explanation, an aryl group, a nonbenzenoid aromatic group, and heteroaromatic group are included in the category of the aromatic group according to the present invention, unless otherwise described.

Among these, as a straight-chain or branched-chain aliphatic group or an alicyclic group that may have a substituent group, straight-chain, branched-chain or cyclic hydrocarbon groups having 1-10 carbons are favorably enumerated, for example. In particular, methyl, ethyl, propyl, isopropyl, butyl, isobutyl, t-butyl, pentyl, isopentyl, hexyl, isohexyl, heptyl, isoheptyl, octyl, isooctyl, nonyl, isononyl, decyl, isodecyl, cyclobutyl, cyclopentyl, cyclohexyl, cycloheptyl, cyclooctyl, cyclononyl, cyclodecyl, etc. are preferable.

As an aromatic group that may have a substituent group, favorably enumerated, for example, are a monocyclic aromatic ring group, a group formed by combining not more than 4 aromatic rings, a group having not more than 5 condensed aromatic rings in which the total number of carbon, oxygen, nitrogen and sulfur is not more than 50.

There is no particular limitation to the monocyclic aromatic ring group, and any suitable group may be selected appropriately depending on a purpose. For example, phenyl, tolyl, xylyl, cumenyl, styryl, mesityl, cinnamyl, phenethyl, and benzhydryl are enumerated. They may also have substituent groups.

There is no particular limitation to the group formed by combining not more than 4 aromatic rings, and any suitable group may be selected appropriately depending on a purpose. For example, naphthyl, anthryl, phenanthryl, indenyl, azulenyl, and benzanthracenyl are enumerated. They may also have substituent groups.

There is no particular limitation to the group having not more than 5 condensed aromatic rings in which the total number of carbon, oxygen, nitrogen and sulfur is not more than 50, and any suitable group may be selected appropriately depending on a purpose. For example, pyrrolyl, furyl, thienyl, pyridyl, quinolyl, isoquinolyl, imidazolyl, pyridinyl, pyrrolopyridinyl, thiazolyl, pyrimidinyl, thiophenyl, indolyl, quinolinyl, pyrinyl, and adenyl are enumerated. They may also have substituent groups.

It is preferable that $R^6$ and $R^7$ in formula (3) are, independently from each other, an aromatic group that may have a substituent group. It is also preferable that $R^{12}$ in formula (6) is an aromatic group that may have a substituent group. The reason is that they provide an organic light-emitting layer forming material that emits blue light with a high color purity, has a high luminous efficiency, and is stable for a long duration of operation, when used singly or as a guest.

These 1,3,6,8-tetrasubstituted pyrene compounds can be applied to cases in which they emit light on their own according to their features, cases in which they emit light as guests by the aid of hosts, and cases in which they play a role of host to assist a guest in emitting light. In the present invention, the term "organic light-emitting layer forming material" means, unless otherwise defined, a material that has at least one of these three functions or a function similar to them, for example, a function to enhance the function of a guest or host.

An organic EL element according to the present invention has an organic light-emitting layer between a positive electrode and negative electrode, in which the organic light-emitting layer contains the above-described 1,3,6,8-tetrasubstituted pyrene compound as an organic light-emitting layer forming material. This organic EL element has features of a high luminous efficiency and a long operation lifetime.

As described above, when a 1,3,6,8-tetrasubstituted pyrene compound according to the present invention is used as an organic light-emitting layer forming material for an organic EL element, there are cases in which an organic light-emitting layer is formed as a single layer of the 1,3,6,8-tetrasubstituted pyrene compound according to the present invention, and cases in which the 1,3,6,8-tetrasubstituted pyrene compound according to the present invention is dispersed as a guest in a host material of an organic light-emitting layer.

When an organic light-emitting layer is formed as a single layer of a 1,3,6,8-tetrasubstituted pyrene compound according to the present invention, the 1,3,6,8-tetrasubstituted pyrene compound according to the present invention is advantageous, since features can be utilized that it is less liable to provide a film with uneven thickness due to crystallization of the like, that, in many cases, it can form a film as a uniform amorphous layer easily, and that it can easily form an organic light-emitting layer that has a high luminous efficiency, and is stable for a long duration of operation, and there is no need of vapor co-deposition with other materials, leading to simplified production processes. However, there may be a case in which decrease in luminous efficiency by concentration quenching may occur that is caused by light-emitting molecules coming closer to each other.

On the other hand, in an organic light-emitting layer with host-guest dispersion, decrease in luminous efficiency by concentration quenching is prevented and a uniform film layer can be formed more easily while maintaining the light emitting characteristics of single molecules, by utilizing a 1,3,6,8-tetrasubstituted pyrene compound as a light-emitting pigment in a mixture with a host material having a larger excitation energy (that is, a material having a light absorption end with a shorter wavelength than that of the 1,3,6,8-tetrasubstituted pyrene compound).

When the wavelength region of the fluorescence emission spectrum of the host material is made to be overlapped with the absorption spectrum of a 1,3,6,8-tetrasubstituted pyrene compound as a guest material in this case, effective transfer of the excitation energy from the host to the guest will be possible, and light emission from the guest material will be realized efficiently with virtually no light emission from the host material. This will lead to a high-purity light emission.

As a host material in a case in which a 1,3,6,8-tetrasubstituted pyrene compound according to the present invention is used as a guest material, enumerated are 4,4'-bis(2,2'-diphenylvinyl)-1,1'-biphenyl (DPVBi) represented by formula (13), a p-sexiphenyl represented by formula (14), 1,3,8,10-tetraphenyl pyrene represented by formula (15), their derivatives, aromatic amine compounds or carbazole compounds, hydroxyquinoline complexes. etc. These compounds may be used singly or in combination.

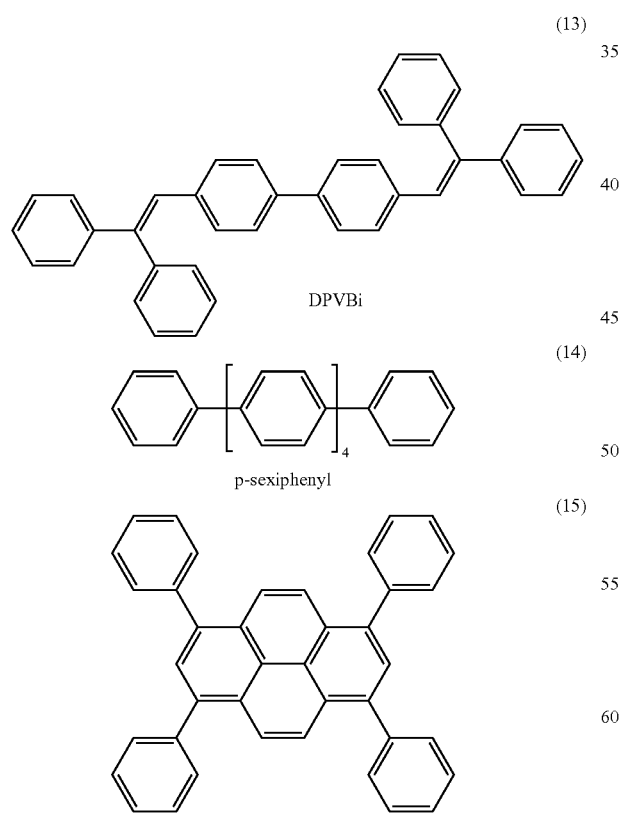

Among these, aromatic amine compounds represented by formula (7) and their derivatives are preferable as the aromatic amine compound. It is to be noted that, in formula (7), $Ar^1$ is a di, tri or tetravalent aromatic group that may have a substituent group. $R^{17}$ and $R^{18}$ are, independently from each other, a monovalent aromatic group that may have a substituent group. n is an integer of 2-4.

Carbazole compounds represented by formula (9) and their derivatives are preferable as the carbazole compound. It is to be noted that, in formula (9), $Ar^2$ is a di, tri or tetravalent aromatic group that may have a substituent group; and $R^{13}$ and $R^{13'}$ are, independently from each other, a hydrogen atom, a halogen atom, or an alkyl, aralkyl, alkenyl, aromatic, cyano, amino, acyl, alkoxycarbonyl, carboxy, alkoxy, alkylsulfonyl, hydroxyl, amide or aromatic oxy group that may have a substituent group. n is an integer of 2-4.

Examples of $Ar^1$ and $Ar^2$ in formula (7) and (9) are the following groups.

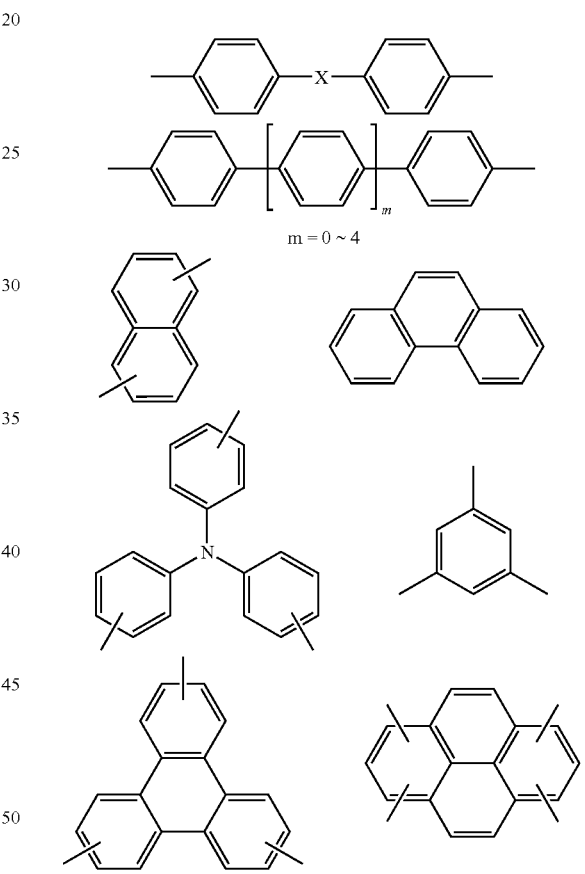

Regarding the above-described groups, the hydrogen atoms may be substituted with other groups. Examples of the divalent bonding group X are as follows.

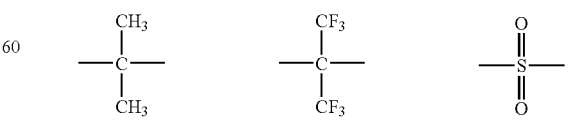

Aromatic amine compounds and carbazole compounds represented by these general formulae are particularly useful as host materials, since the interaction with a 1,3,6,8-tetrasubstituted pyrene compound according to the present invention is small, and accordingly has little influence on the light-emitting properties intrinsic to the 1,3,6,8-tetrasubstituted pyrene compound, when mixed with it.

N,N'-dinaphthyl-N,N'-diphenyl-[1,1'-biphenyl]-4,4'-diamine (NPD) represented by formula (8) is an example of an aromatic amine compound represented by formula (7), and 4,4'-bis(9-carbazolyl)-biphenyl (CBP) represented by formula (10) is an example of a carbazole compound represented by formula (9).

Also, as a hydroxyquinoline complex, hydroxyquinoline-oxyaryl complexes and their derivatives represented by formula (11) are preferable. It is to be noted that, in formula (11), $R^{14}$ is hydrogen or an alkyl group that may have a substituent group, and $R^{15}$ is an aromatic group that may have a substituent group. M is a trivalent metal. n is 1 or 2.

A more concrete example of a hydroxyquinoline-oxyaryl complex represented by formula (11) is an aluminum hydroxyquinoline-oxybiphenyl complex (BAlq) represented by formula (12).

It is to be noted that, when a host material such as described above is used, it is possible to make an organic light-emitting layer also have a function of a positive hole transporting layer or an electron transporting layer, thus serving as a positive hole transporting and organic light-emitting layer (that is, a positive hole transporting-cum-organic light-emitting layer) or an organic light-emitting and electron transporting layer (that is, organic light-emitting-cum-electron transporting layer). Aromatic amine compounds can serve to function as a positive hole transporting layer, and carbazole compounds as well as hydroxyquinoline-oxyaryl complexes can serve to function as an electron transporting layer.

A 1,3,6,8-tetrasubstituted pyrene compound according to the present invention can be used not as a guest but as a host material in an organic light-emitting layer of an organic EL element. As a guest material to be mixed in the organic light emitting layer, those materials emitting light having a wavelength longer than that of the 1,3,6,8-tetrasubstituted pyrene compound according to the present invention are used. The following materials are the examples.

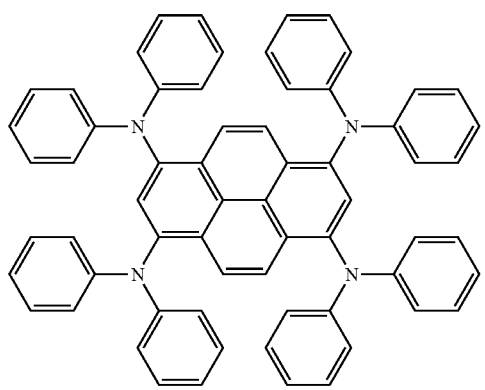

1,3,6,8-tetrakis(diphenylamino)pyrene (green light emission)

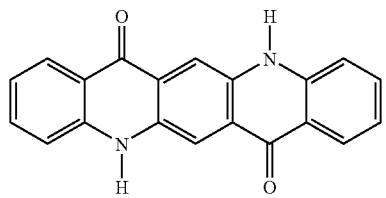

quinacridone (green light emission)

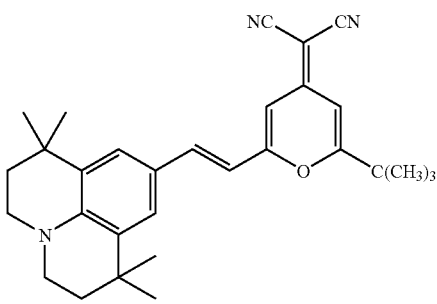

DCJTB 4-dicyanomethylene-6-cp-julolidinostyryl-2-tert-butyl-4H-pyran (Red Light Emission)

There is no particular limitation to the method for manufacturing a 1,3,6,8-tetrasubstituted pyrene compound according to the present invention, and any suitable method may be appropriately selected from among the known methods depending on a purpose. For example, the following methods may be favorably used.

A 1,3,6,8-tetrahalogenated pyrene is synthesized by the reaction of 1 equivalent of pyrene and 4 equivalents of halogen. Tetrahalogenation tends to occur at the 1,3,6 and 8 positions, in accordance with the reactivity of pyrene. For the halogenation, methods similar to the general halogenation method of aromatic hydrocarbons, that is, those in which a halogen as a simple substance is added to pyrene dissolved in a solvent, are preferable. Chlorine, bromine, and iodine are advantageous as a halogen for the reactions in the subsequent steps. Chlorine and bromine are particularly favorable due to their ease for the halogenation reaction.

Next, a 1,3,6,8-tetrahalogenated pyrene and a boronic acid derivative corresponding to a desired compound are heated in the presence of a catalyst and a base to form a 1,3,6,8-tetra-substituted pyrene compound according to the present invention, by the reaction known as "Suzuki Coupling". The reaction route is shown below.

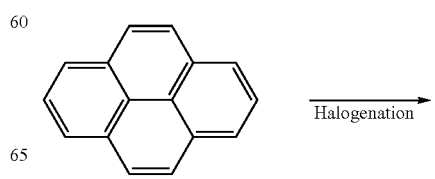

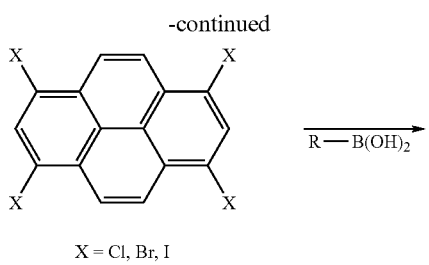

X = Cl, Br, I

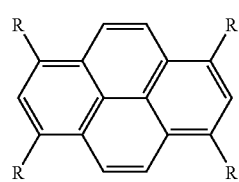

In the above-described formula, R has the same meaning as R in formula (1). In the formula, the intermediate and final product may be used in a state of a mixture.

As the catalyst, a palladium compound such as tetrakis(triphenylphosphine)palladium (0) may be utilized. As a base, sodium carbonate, potassium carbonate, sodium hydroxide, a sodium alkoxide such as sodium-t-butoxide, etc. may be used.

The following are examples of a boronic acid derivative [R—B(OH)$_2$] that is applicable to this reaction. Mixtures may be used. Hereupon, a line with no chemical group on its end means a methyl group in the following formulae.

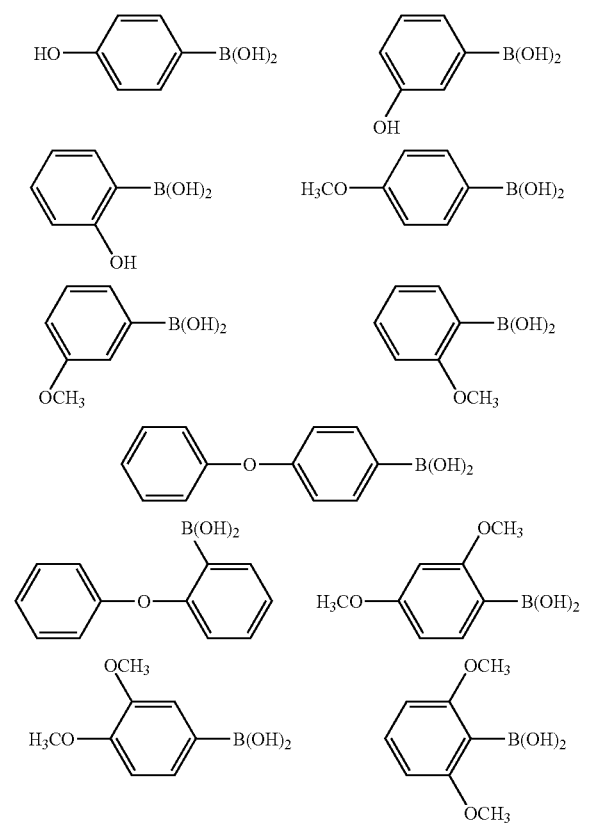

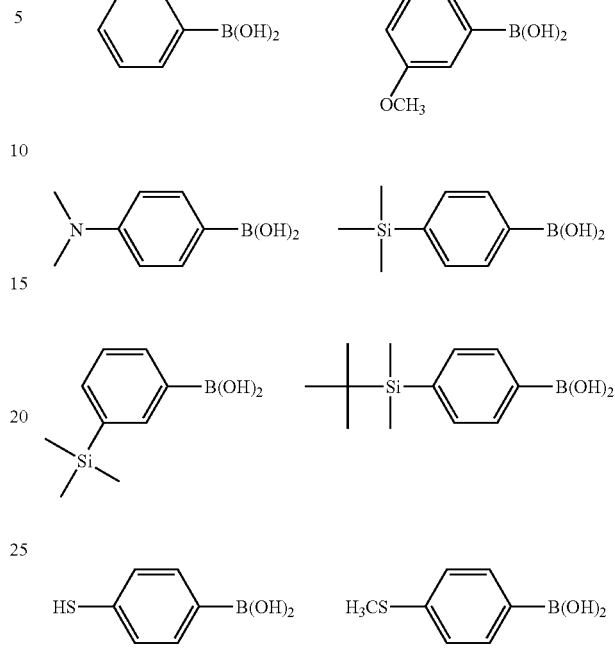

It is to be noted that a 1,3,6,8-tetrasubstituted pyrene compound according to the present invention may be obtained by synthesizing a 1,3,6,8-tetrakis(chlorinated-phenyl)pyrene by Suzuki coupling of a 1,3,6,8-tetrahalogenated pyrene and a chlorinated-phenyl boronic acid, and carrying out an amination reaction in the presence of a catalyst and a base. From the viewpoint of reactivity, bromine or iodine are preferable as a halogen for a 1,3,6,8-tetrahalogenated pyrene that is a starting material. The reaction route is shown in the following formula.

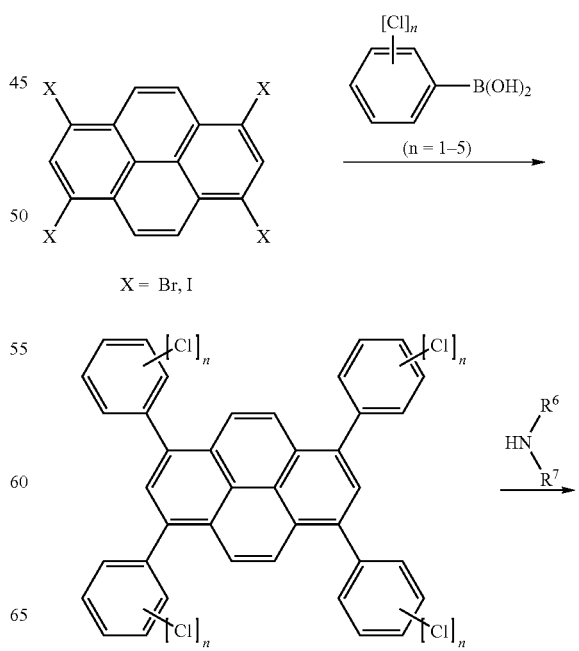

-continued

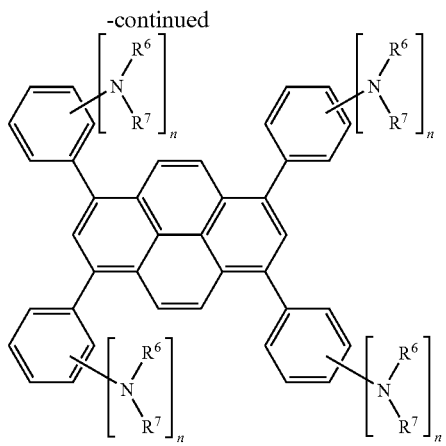

In the above-described formula, $R^6$ and $R^7$ have the same meanings as $R^6$ and $R^7$ in formula (3). Also in the above-described formula, n indicates the number of chlorine or amino substituent groups, and is, independently from each other, an integer of 1-5. In the above-described formula, the intermediate and final product may be used in a state of a mixture.

As the catalyst for the amination reaction, a palladium compound such as a palladium-tributylphophine complex, or a copper powder may be utilized. As a base, sodium carbonate, potassium carbonate, sodium hydroxide, a sodium alkoxide such as sodium-t-butoxide, etc. may be used.

The following materials are examples of a chlorinated-phenylboronic acid that is applicable to this reaction.

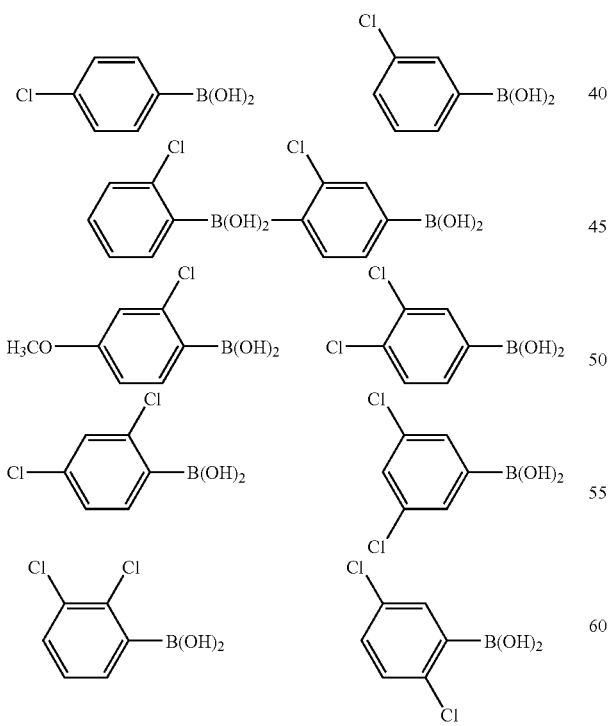

The following materials are examples of an amine that is applicable to this reaction.

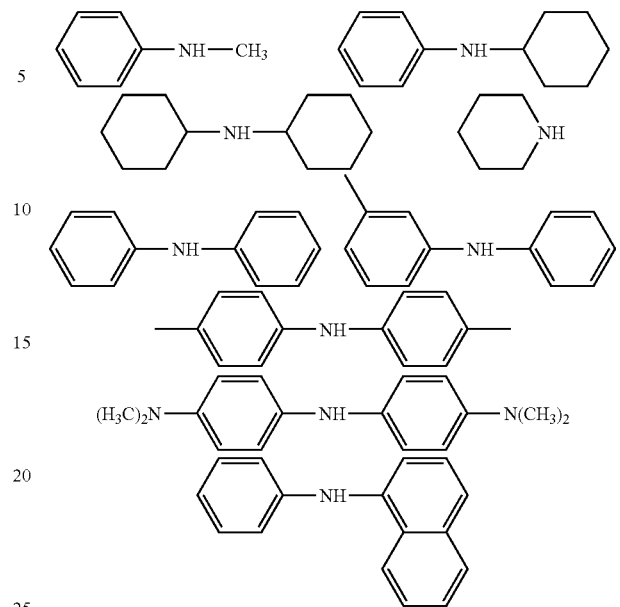

An organic EL element has a structure of a positive hole injection layer, a positive hole transporting layer, an organic light-emitting layer, an electron transporting layer, and an electron injection layer sandwiched between a positive electrode and a negative electrode. Of these, the positive hole injection layer, the positive hole transporting layer, the electron transporting layer, and the electron injection layer may not be present. Other layers may be included. One layer may have a plurality of functions. Generally, these layers are formed on a transparent substrate such as glass. This transparent substrate may be included in an organic EL element according to the present invention.

The following are examples of the structures of layers.

Positive electrode/positive hole injection layer/positive hole transporting layer/organic light-emitting layer/ electron transporting layer/electron injection layer/ negative electrode.

Positive electrode/positive hole injection layer/positive hole transporting layer/organic light-emitting layer/ electron transporting layer/negative electrode.

Positive electrode/positive hole transporting layer/organic light-emitting layer/electron transporting layer/electron injection layer/negative electrode.

Positive electrode/positive hole transporting layer/organic light-emitting layer/electron transporting layer/negative electrode.

Positive electrode/positive hole injection layer/positive hole transporting layer/organic light-emitting and electron transporting layer/electron injection layer/negative electrode.

Positive electrode/positive hole injection layer/positive hole transporting layer/organic light-emitting and electron transporting layer/negative electrode.

Positive electrode/positive hole transporting layer/organic light-emitting and electron transporting layer/electron injection layer/negative electrode.

Positive electrode/positive hole transporting layer/organic light-emitting and electron transporting layer/negative electrode.

Positive electrode/positive hole injection layer/positive hole transporting and organic light-emitting layer/electron transporting layer/electron injection layer/negative electrode.

Positive electrode/positive hole injection layer/positive hole transporting and organic light-emitting layer/electron transporting layer/negative electrode.

Positive electrode/positive hole transporting and organic light-emitting layer/electron transporting layer/electron injection layer/negative electrode.

Positive electrode/positive hole transporting and organic light-emitting layer/electron transporting layer/negative electrode.

Positive electrode/positive hole transporting and electron transporting and organic light-emitting layer/negative electrode.

In the following, materials, thicknesses and manufacturing methods for the respective layers are described.

Positive Electrode

There is no particular limitation to the material for the positive electrode, and any suitable material may be appropriately selected depending on a purpose. For example, metals, alloys, metal oxides, electroconductive compounds, mixtures thereof, etc. are enumerated. Among these, materials with a work function of not less than 4 eV are preferable.

As concrete examples of a material for the positive electrode, enumerated are electroconductive metal oxides such as tin oxide, zinc oxide, indium oxide, and indium-tin oxide (ITO), metals such as gold, silver, chromium and nickel, mixtures or layered products of these metals and electroconductive metal oxides, inorganic electroconductive materials such as copper iodide and copper sulfide, organic electroconductive materials such polyaniline, polythiophene and polypyrrole, layered products of these materials and ITO, etc. They may be used singly, or two or more of them may be used in combination. Of these, electroconductive metal oxides are preferable, and ITO is particularly preferable from the viewpoint of productivity, high electroconductivity, transparency, etc.

There is no particular limitation to the thickness of the positive electrode, and any suitable thickness may be appropriately selected depending on a material for use, or the like. A thickness of 1-5,000 nm is preferable, and a thickness of 20-200 nm is more preferable.

A positive electrode is usually formed on a substrate made of glass such as soda lime glass and non-alkali glass, a transparent resin, or the like. When glass is used for a substrate, non-alkali glass, silica, and barrier-coated soda-lime glass are preferable from the viewpoint of decreasing ions eluted from the glass.

There is no particular limitation to the thickness of the substrate as long as it is thick enough to maintain the mechanical strength. When glass is used as the substrate, it is usually not less than 0.2 mm, and is preferably not less than 0.7 mm.

A positive electrode may be favorably formed, for example, by a vapor deposition method, wet film forming method, electron beam method, sputtering method, reactive sputtering method, MBE (molecular beam epitaxy) method, cluster ion beam method, ion plating method, plasma polymerization method (high frequency excited ion plating method), molecule laminating method, printing method, transfer method, method for applying dispersed materials such as ITO by a chemical reaction method (sol-gel method), etc.

Decrease in the driving voltage and increase in the luminous efficiency of an organic EL element are also possible by carrying out cleaning and other treatments of the positive electrode. Regarding the other treatments, when the material for the afore-mentioned positive electrode is ITO for example, UV-ozone treatment, plasma treatment, etc. are favorably enumerated.

Positive Hole Injection Layer

There is no particular limitation to the material for the positive hole injection layer, and any suitable material may be appropriately selected depending on a purpose. For example, a star-burst amine (4,4',4"-tris[3-methylphenyl (phenyl) amino]triphenylamine, m-MTDATA) represented by the following formula, copper phthalocyanine, polyaniline, etc. are favorably enumerated.

There is no particular limitation to the thickness of the positive hole injection layer, and any suitable thickness may be appropriately selected depending on a purpose. For example, a thickness of about 1-100 nm is preferable, and a thickness of 5-50 nm is more preferable.

The positive hole injection layer can be preferably formed, for example, by a vapor deposition method, wet film forming method, electron beam method, sputtering method, reactive sputtering method, MBE method, cluster ion beam method, ion plating method, plasma polymerization method (high frequency excited ion plating method), molecule laminating method, LB method, printing method, transfer method, etc.

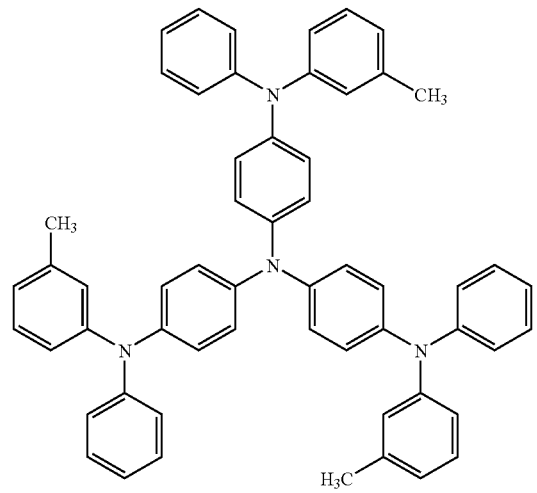

Positive Hole Transporting Layer

There is no particular limitation to the material for the positive hole transporting layer, and any suitable material may be appropriately selected depending on a purpose. For example, electroconductive oligomers and polymers such as aromatic amine compounds, carbazole compounds, imidazole compounds, triazole compounds, oxazole compounds, oxadiazole compounds, polyarylalkanes, pyrazoline compounds, pyrazolone compounds, phenylenediamine, aryl amines, amino-substituted chalcones, styrylanthracene, fluorenone, hydrazone, stilbene, silazane, styrylamine, aromatic dimethylidene compounds, porphyrin compounds, polysilane compounds, poly(N-vinylcarbazole), aniline copolymers, thiophene oligomers and polymers, and polythiophene, as well as a carbon film and other similar materials are enumerated. It is to be noted that a positive hole transporting and light emitting layer may be formed by mixing, to form a film, such a material for a positive hole transporting layer with a material for a light emitting layer.

These materials may be used singly, or two or more materials may be used in combination. Of these, aromatic amine compounds are preferable. Specifically, aromatic amines such as N,N'-diphenyl-N,N'-bis(3-methylphenyl)-[1,1'-biphenyl]-4,4'-diamine (TPD) and NPD as shown in the following formulae are more preferable.

There is no particular limitation to the thickness of the positive hole transporting layer, and any suitable thickness may be appropriately selected depending on a purpose. Generally, it is in a range of 1-500 nm, and a thickness of 10-100 nm is preferable.

A positive hole transporting layer can be formed in ways similar to those for a positive hole injection layer, with appropriately changing raw materials and conditions.

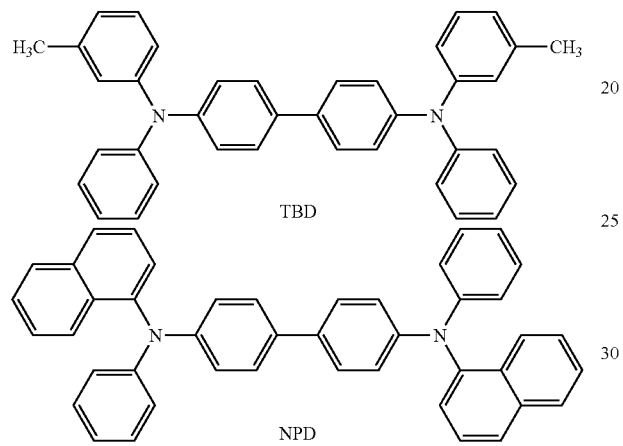

TBD

NPD

Electron Transporting Layer

There is no particular limitation to the material for the electron transporting layer, and any suitable material may be appropriately selected depending on a purpose. For example, hydroxyquinoline complexes such as tris(8-quinolinolate) aluminum (Alq) represented by the following formula, hydroxyquinoline-oxyaryl complexes such as BAlq, oxadiazole compounds, triazole compounds, phenanthroline compounds, perylene compounds, pyridine compounds, pyrimidine compounds, quinoxaline compounds, diphenyl quinone compounds, nitro-substituted fluorene compounds, etc. are enumerated. It is to be noted that a light emitting and electron transporting layer may be formed by mixing, to form a film, a material for such an electron transporting layer with a material for a light emitting layer, and a positive hole transporting and light emitting and electron transporting layer may be formed by further mixing, to form a film, a material for a positive hole transporting layer.

There is no particular limitation to the thickness of the electron transporting layer, and any suitable thickness may be appropriately selected depending on a purpose. For example, it is generally in a range of about 1-500 nm, and a thickness of 10-50 nm is preferable.

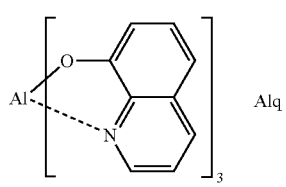

Alq

An electron transporting layer may be composed of two or more layers. In such a case, it is desirable to use, for an electron transporting layer adjacent to an organic light emitting layer, a material having a light absorption end that is shorter in wavelength than that of a 1,3,6,8-tetrasubstituted pyrene compound according to the present invention, since it makes it possible to limit the light emitting region in the organic EL element to the organic light emitting layer, and accordingly, it can prevent undesirable light emission from the electron transporting layer.

As such a material having a light absorption end that is shorter in wavelength than that of a 1,3,6,8-tetrasubstituted pyrene compound according to the present invention, enumerated are hydroxyquinoline-oxyaryl complexes, phenanthroline compounds, oxadiazole compounds, triazole compounds, 8-quinolinol compounds, organic metal complexes having such a compound as a ligand, etc. BAlq and compounds represented by the following formulae are particularly preferable.

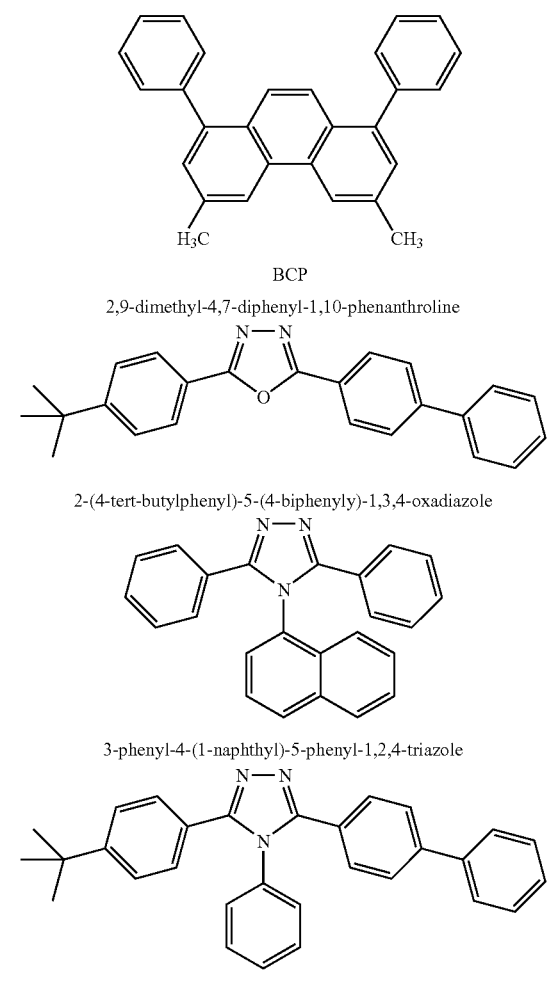

BCP
2,9-dimethyl-4,7-diphenyl-1,10-phenanthroline 2-(4-tert-butylphenyl)-5-(4-biphenyly)-1,3,4-oxadiazole 3-phenyl-4-(1-naphthyl)-5-phenyl-1,2,4-triazole 2-(4-tert-butylphenyl)-4-phenyl-5-(4'-biphenylyl)-1,2,4-triazole It is to be noted that the three branches without any chemical group at the ends means a tert-butyl group in the above-described formulae.

An electron transporting layer can be formed in ways similar to those for a positive hole injection layer, with appropriately changing raw materials and conditions.

Electron Injection Layer

There is no particular limitation to the material for the electron injection layer, and any suitable material may be appropriately selected depending on a purpose. For example, alkali metal fluorides such as lithium fluoride, alkaline-earth metal fluorides such as strontium fluoride, etc. may be favorably used. There is no particular limitation to the thickness of the electron injection layer, and any suitable thickness may be appropriately selected depending on a purpose. For example, it is generally in a range of about 0.1-10 nm, and a thickness of 0.5-2 nm is preferable.

An electron injection layer may be favorably formed, for example, by a vapor deposition method, electron beam method, sputtering method, etc.

Negative Electrode

There is no particular limitation to the material for the negative electrode, and any suitable material may be appropriately selected depending on the adhesiveness to adjacent layers or molecules such as the electron transporting layer and the light emitting layer, ionization potential, stability, etc. For example, metals, alloys, metal oxides, electroconductive compounds, mixtures thereof, etc. are enumerated.

As concrete examples of a material for the negative electrode, alkali metals (Li, Na, K, and Cs, for example), alkaline-earth metals (Mg and Ca, for example), gold, silver, lead, aluminum, alloys or mixed metals of sodium-potassium, alloys or mixed metals of lithium-aluminum, alloys or mixed metals of magnesium-silver, rare earth metals such as indium and ytterbium, alloys thereof, etc. are enumerated. These materials may be used singly, or two or more materials may be used in combination. Of these, materials having a work function of not more than 4 eV are preferable, and aluminum, alloys or mixed metals of lithium-aluminum, alloys or mixed metals of magnesium-silver, etc. are more preferable.

There is no particular limitation to the thickness of the negative electrode, and any suitable thickness may be appropriately selected depending on the material for a negative electrode, etc. A thickness of 1-10,000 nm is preferable, and a thickness of 20-200 nm is more preferable.

A negative electrode may be favorably formed, for example, by a vapor deposition method, wet film forming method, electron beam method, sputtering method, reactive sputtering method, MBE method, cluster ion beam method, ion plating method, plasma polymerization method (high frequency excited ion plating method), printing method, transfer method, etc.

When two or more materials are used for a negative electrode, the two or more materials may be deposited concomitantly to form an alloy electrode or the like, or a previously prepared alloy may be used for deposition to form such an alloy electrode or the like.

Other Layers

An organic EL element according to the present invention may have other layers appropriately selected depending on a purpose. As the other layers, a positive hole blocking layer and a protective layer are preferably enumerated, for example.

A positive hole blocking layer is arranged between a light emitting layer and an electron transporting layer. When an organic EL element has a positive hole blocking layer, the positive hole which has been transported from the positive electrode side is blocked by the positive hole blocking layer, and the electron which has been transported from the negative electrode passes through the positive hole blocking layer to reach the light emitting layer, thus enabling efficient recombination of positive holes and electrons in the light emitting layer. This will prevent the recombination of positive holes and electrons in the organic thin film layers other than the light emitting layer, resulting in efficient light emission of the light emitting pigment for the purpose, and will be advantageous from the viewpoints of color purity, etc. There is no particular limitation to the material for the positive hole blocking layer, and any suitable material may be appropriately selected from the same materials as for the electron transporting layer, depending on a purpose.

There is no particular limitation to the thickness of the positive hole blocking layer, and any suitable thickness may be appropriately selected depending on a purpose. For example, it is usually in a range of about 1-500 nm, and a thickness of 10-50 nm is preferable. The positive hole blocking layer may be of a single-layered structure, or of a multi-layered structure.

The positive hole blocking layer may be favorably formed, for example, by a vapor deposition method, wet film forming method, electron beam method, sputtering method, reactive sputtering method, MBE method, cluster ion beam method, ion plating method, plasma polymerization method (high frequency excited ion plating method), molecule laminating method, LB method, printing method, transfer method, etc.

A protective layer is a layer to protect the organic EL element from the environmental influence, and is formed so that it envelops the laminate composed of the above-described respective layers. There is no particular limitation to the material for the protective layer, and any suitable material may be appropriately selected depending on a purpose. For example, preferable are those materials that can prevent molecules and substances that accelerate degradation of the organic EL element such as water and oxygen, from intruding into the organic EL element.

As a material for the protective layer, for example, metals such as In, Sn, Cu, Al, Ti, Ni, metal oxides such as MgO, SiO, $SiO_2$, $Al_2O_3$, GeO, NiO, CaO, BaO, $Fe_2O_3$, $Y_2O_3$ and $TiO_2$, nitrides such as SiN, $SiN_xO_y$, metal fluorides such as $MgF_2$, LiF, $AlF_3$ and $CaF_2$, polyethylene, polypropylene, polymethyl methacrylate, polyimide, polyurea, polytetrafluoroethylene, polychlorotrifluoroethylene, polydichlorodifluoroethylene, copolymers of chlorotrifluoroethylene and dichlorofluroethylene, copolymers obtained by copolymerizing monomer mixtures comprising tetrafluoroethylene and at least one comonomer, fluorine-containing copolymers having a cyclic structure in the copolymeric main chain, water-absorbing materials having a water absorption of not less than 1% by weight, dampproof materials having a water absorption of not more than 0.1% by weight, etc. are enumerated.

A protective layer may be favorably formed, for example, by a vapor deposition method, wet film forming method, sputtering method, reactive sputtering method, MBE method, cluster ion beam method, ion plating method, plasma polymerization method (high frequency excited ion plating method), printing method, transfer method, etc.

Hereupon, an organic light-emitting layer can be formed by known methods. For example, it can be favorably formed by a vapor deposition method such as vacuum vapor deposition, wet film forming method, MBE method, cluster ion beam method, molecule laminating method, LB method, printing method, transfer method, etc. Of these, a vapor deposition method is preferable, since no organic solvent is used, thus requiring no waste water treatment, and the organic light-emitting layer can be manufactured conveniently and efficiently at a low cost. However, when a light-emitting layer is designed in a monolayer structure, for example, as a positive hole transporting and light-emitting and electron transporting layer, a wet film forming method is also preferable.

There is no particular limitation to the vapor deposition method, and any suitable method may be appropriately selected from known methods depending on a purpose. For example, a vacuum vapor deposition method, resistance heating vapor deposition method, chemical vapor deposition method, physical vapor deposition method, etc. are enumerated. As a chemical vapor deposition method, for example, a plasma CVD method, laser CVD method, thermal CVD method, gas source CVD method, etc. are enumerated.

Regarding the wet film forming method, it is also possible to mix a binder comprising materials such as a host and/or a polymer, and a 1,3,6,8-tetrasubstituted pyrene compound according to the present invention in a solvent, and apply a wet film forming method such as a spin coating method, ink-jet method, dip coating method, blade coating method, etc. If the above-described materials enumerated as materials for a positive hole transporting layer and an electron transporting layer, are mixed concomitantly into the solution for film forming during the process, in order to enhance the charge transportability of the organic light emitting layer, the functions of a positive hole transporting layer and electron transporting layer may be added to the organic light emitting layer, so that a single layer for positive hole transportation and organic light emission, a single layer for organic light emission and electron transportation, or a single layer for positive hole transportation, organic light emission and electron transportation, is formed.

As a binder usable in such a case, polyvinylcarbazole, polycarbonate, polyvinyl chloride, polystyrene, polymethyl methacrylate, polyesters, polysulfone, polyphenylene oxide, polybutadiene, hydrocarbon resins, ketone resins, phenoxy resins, polyamides, ethyl cellulose, vinyl acetate, acrylonitrile-butadiene-styrene resins, polyurethane, melamine resins, unsaturated polyester resins, alkyd resins, epoxy resins, silicone resins, etc. are enumerated.

An organic EL display using an organic EL element according to the present invention has a high luminous efficiency and a long operation lifetime, and can be operated stably. This organic EL element can be used as a passive matrix panel or an active matrix panel (for example, Nikkei Electronics, March 13, vol. 765, p. 55-62, 2000).

As a colorization method of organic EL displays, there are a three-color light emitting method in which organic EL element parts exhibiting three colors, red, green and blue, respectively, are placed on a substrate, a white light method in which white light of a white light emitting organic EL element is passed through color filters to be divided into three primary colors, a color conversion method in which blue light of a blue light emitting organic EL element is passed through fluorescent pigment layers to be converted to red and green colors, etc (for example, "Monthly Display", September, p. 33-37, 2000). Of these, a 1,3,6,8-tetrasubstituted pyrene compound according to the present invention can be favorably used for a blue light emitting organic EL element part of an organic EL display by the three color emitting method, when it is used singly or as a guest.

In a panel by the three color emitting method, organic EL element parts emitting red, green and blue colors respectively are necessary. In such a case, the following combinations are examples for the respective light emitting element parts.

Blue Light Emitting Element Part

A structure as shown in examples below in which a 1,3,6,8-tetrasubstituted pyrene compound according to the present invention is used singly or as a guest (see EXAMPLES).

Green Light Emitting Element Part

ITO (positive electrode)/NPD (positive hole transporting layer)/Alq (electron transporting and light emitting layer)/Al—Li (negative electrode).

Red Light Emitting Element Part

ITO (positive electrode)/NPD (positive hole transporting layer)/Alq containing 1% by weight of 4-dicyanomethylene-6-cp-julolidinostyryl-2-tert-butyl-4H-pyran (DCJTB) represented by the following formula (electron transporting and organic light emitting layer)/Al—Li (negative electrode).

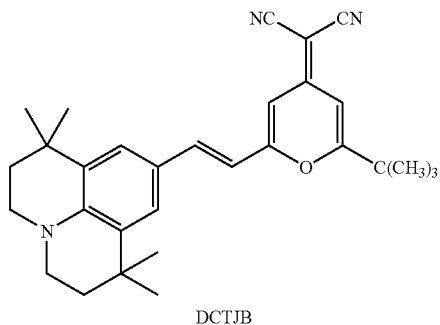

DCTJB 4-dicyanomethylene-6-cp-julolidinostyryl-2-tert-butyl-4H-pyran

An organic EL element according to the present invention may be used for a passive matrix display and an active matrix display. FIG. 1 illustrates an example of an organic EL element according to the present invention used for a passive matrix display, in which a structure of positive electrode/positive hole transporting layer/organic light-emitting layer/electron transporting layer/negative electrode is shown. In FIG. 1, the organic EL element is formed by layering, on a glass substrate 1, a positive electrode 2 made of ITO, positive hole transporting layer 3, organic light-emitting layer 4, electron transporting layer 5, and negative electrode 6 made of a metal. The positive electrode 2 made of ITO is a row electrode, and the negative electrode 6 made of a metal is a column electrode. In this figure, red light 7, green light 8 and blue light 9 are realized by changing organic light-emitting layer forming materials used for the organic light emitting layer 4.

Figure 2:
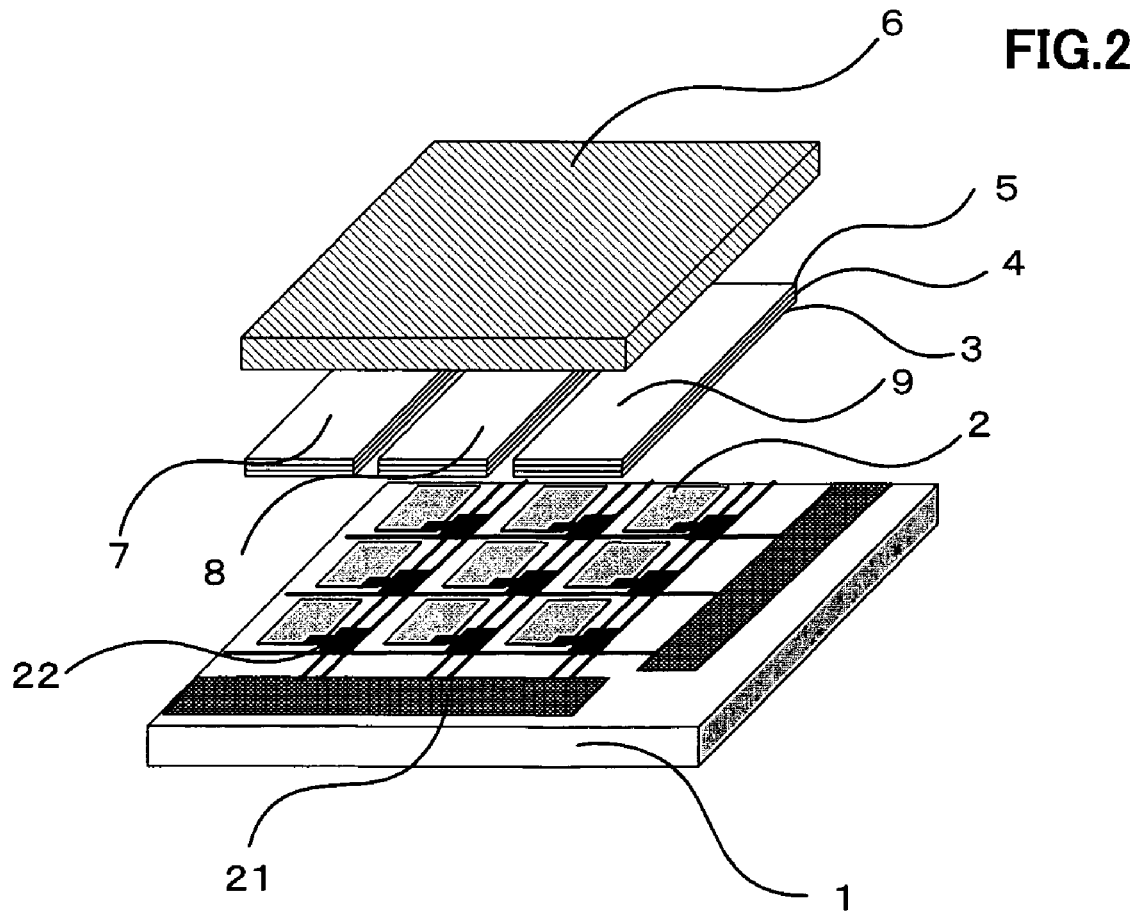
FIG. 2 is a schematic perspective view showing an organic EL element according to the present invention that is used in an active matrix display.

FIG. 2 illustrates an organic EL element according to the present invention used for an active matrix display. FIG. 2 also shows an example of structure of positive electrode/positive hole transporting layer/organic light-emitting layer/electron transporting layer/negative electrode. In FIG. 2, the organic EL element is formed by layering, on a glass substrate 1, a driving circuit 21, TFT (thin film transistor) circuit 22, positive electrode 2 made of ITO, positive hole transporting layer 3, organic light-emitting layer 4, electron transporting layer 5, and negative electrode 6 made of a metal. In this figure, too, red light 7, green light 8 and blue light 9 are realized by changing organic light-emitting layer forming materials used for the organic light emitting layer 4.

Next, examples and comparative examples of the present invention are explained in detail.

EXAMPLE 1

Synthesis of 1,3,6,8-tetra(4-phenoxyphenyl)pyrene Represented by the Formula Below

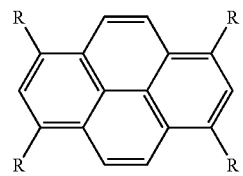

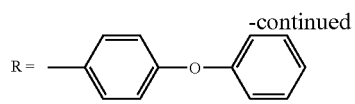

1,3,6,8-tetrabromopyrene was obtained by the reaction of one equivalent of pyrene and 4 times as much as bromine in equivalent in a nitrobenzene, according to the method described in Annalen der Chemie, vol. 531, p. 81.

Next, 4.4 equivalents of 4-phenoxyphenylboronic acid, 10 equivalents of sodium carbonate in a 2 mol/L aqueous solution, and 0.12 equivalents of tetrakis(triphenylphosphine)palladium (0) were added to one equivalent of 1,3,6,8-tetrabromopyrene, and the mixture was subjected to heating under refluxing to allow reaction for three hours, using benzene as a solvent.

After cooling the reaction product, the deposit formed by adding methanol to the reaction product was washed with water, and recrystallized from THF-methanol to obtain a crude product. The crude product was purified by sublimation in vacuo, to form a compound for the purpose.

An o-xylene solution of the compound showed a strong blue fluorescence, by irradiating with ultraviolet rays having a wavelength of 365 nm. The molecular weight of the compound by the mass spectrum was 850, coinciding with the expected value for the molecular formula ($C_{62}H_{42}O_4$).

EXAMPLE 2

Synthesis of 1,3,6,8-tetrakis[3-(3-methyldiphenylamino)phenyl]pyrene shown in the following formula

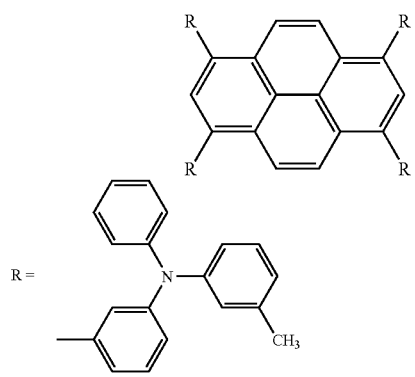

4.4 equivalents of 3-chlorophenylboronic acid, 10 equivalents of sodium carbonate in a 2 mol/L aqueous solution, and 0.12 equivalents of tetrakis(triphenylphosphine)palladium (0) were added to one equivalent of 1,3,6,8-tetrabromopyrene obtained in the same way as for EXAMPLE 1, and the mixture was subjected to heating under refluxing to allow reaction for three hours, using benzene as a solvent. 1,3,6,8-tetra(3-chlorophenyl)pyrene was obtained after deposition and purification through recrystallization of the product.

4.4 equivalents of 3-methyldiphenylamine, 10 equivalents of sodium tert-butoxide, 0.01 equivalent of palladium acetate, and 0.04 equivalents of tri-tert-butyl phosphine were added to this 1,3,6,8-tetra(3-chlorophenyl)pyrene in an amount of one equivalent, and the mixture was subjected to heating under refluxing to allow reaction for three hours, using o-xylene as a solvent.

After cooling the reaction product, the deposit formed by adding methanol to the reaction product was washed with water, and recrystallized from THF-methanol to obtain a crude product. The crude product was purified by sublimation in vacuo, to form a compound for the purpose.

An o-xylene solution of the compound showed a strong blue fluorescence, by irradiating with ultraviolet rays having a wavelength of 365 nm. The molecular weight of the compound by the mass spectrum was 1,230, coinciding with the expected value for the molecular formula ($C_{92}H_{70}N_4$).

EXAMPLE 3

Synthesis of 1,3,6,8-tetrakis[3,5-bis(3-methyldiphenylamino)phenyl]pyrene shown in the following formula

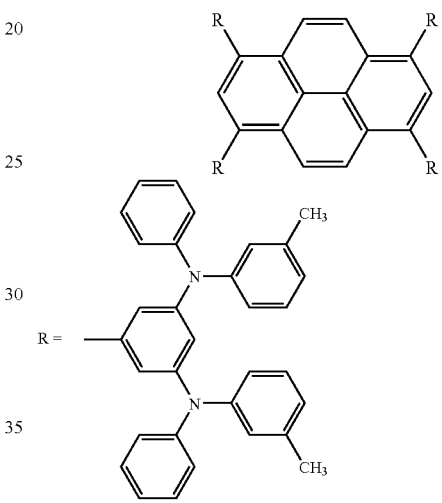

According to the same processes as for EXAMPLE 2, except that 3,5-dichlorophenylboronic acid was used instead of 3-chlorophenylboronic acid, and 8.8 equivalents of 3-methyldiphenylamine was used instead of 4.4 equivalents, 1,3,6,8-tetrakis[3-(3-methyldiphenylamino)phenyl]pyrene was obtained.

Figure 4:
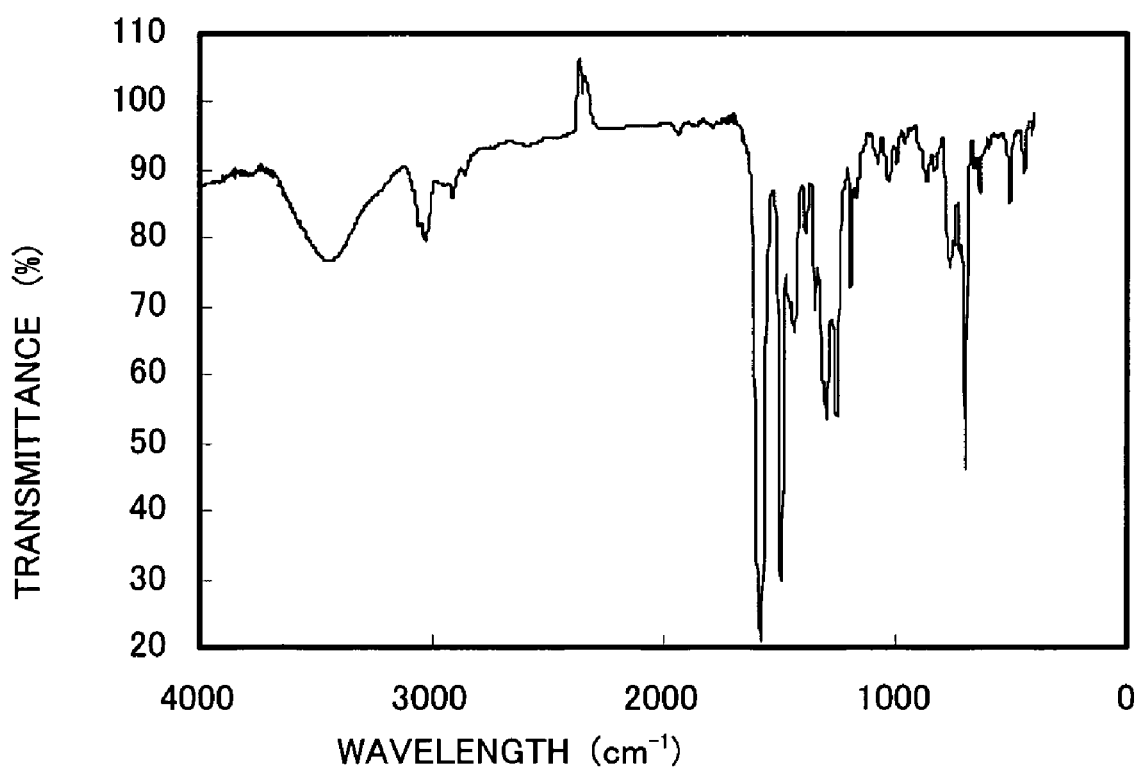
FIG. 4 is an IR spectrum of 1,3,6,8-tetrakis[3-(3-methyl-diphenylamino)phenyl]pyrene obtained in EXAMPLE 3.

An o-xylene solution of the compound showed a strong blue fluorescence, by irradiating with ultraviolet rays having a wavelength of 365 nm. The molecular weight of the compound by the mass spectrum was 1,954, coinciding with the expected value for the molecular formula ($C_{144}H_{114}N_8$). The IR spectrum of the compound in KBr is shown in FIG. 4.

EXAMPLE 4

(Manufacturing of a Layered Organic EL Element)

A layered organic EL element was manufactured using 1,3,6,8-tetra(4-phenoxyphenyl)pyrene as an organic light emitting layer, as described below.

A glass substrate with an ITO electrode thereon was washed with water, acetone and isopropyl alcohol, and each layer was layered on the substrate, using a vacuum vapor deposition apparatus $1.33 \times 10^{-4}$ Pa), with the substrate being at room temperature).

Figure 3:
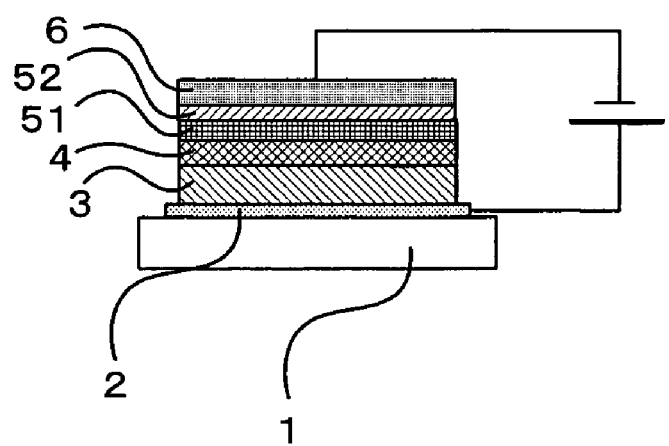
FIG. 3 is a schematic cross-sectional view of an organic EL element.

Specifically, as shown in FIG. 3, a 50 nm-thick, positive hole transporting layer 3 of NPD, a 20 nm-thick, organic light emitting layer 4 made of 1,3,6,8-tetra(4-phenoxyphenyl) pyrene, a 10 nm-thick, first electron transporting layer 51 made of BAlq, a 20 nm-thick, second electron transporting layer 52 made of Alq, and further, a 50 nm-thick, negative electrode 6 made of an Al—Li alloy (Li: 0.5% by weight) were sequentially deposited on the glass substrate 1 with an ITO electrode 2 thereon.

When voltage was applied between the ITO as a positive electrode and the Al—Li as a negative electrode of the organic EL element, blue light emission was observed at a voltage not less than 5 V. Blue light emission having a luminescence intensity of 1,470 cd/m$^2$ was observed at an applied voltage of 10 V.

EXAMPLE 5

An organic EL element was manufactured as in EXAMPLE 4, except that a layer that was obtained by concomitant vapor deposition of 1,3,6,8-tetra(4-phenoxyphenyl)pyrene and NPD was used instead of a 1,3,6,8-tetra(4-phenoxyphenyl)pyrene layer as an organic light emitting layer. The NPD acted as a host. It is considered that the layer was a positive hole transporting and organic light emitting layer. The weight-based ratio of vapor deposition rates was set to 10 of 1,3,6,8-tetra(4-phenoxyphenyl)pyrene to 90 of NPD.

When voltage was applied between the ITO as a positive electrode and the Al—Li as a negative electrode of the organic EL element, blue light emission was observed at a voltage not less than 4 V. Blue light emission having a luminescence intensity of 3,600 cd/m$^2$ was observed at an applied voltage of 10 V.

EXAMPLE 6

An organic EL element was manufactured as in EXAMPLE 4, except that a layer that was obtained by concomitant vapor deposition of 1,3,6,8-tetra(4-phenoxyphenyl)pyrene and CBP was used instead of a 1,3,6,8-tetra(4-phenoxyphenyl)pyrene layer as an organic light emitting layer. The CBP acted as a host. It is considered that the layer was an organic light emitting and electron transporting layer. The weight-based ratio of vapor deposition rates was set to 10 of 1,3,6,8-tetra(4-phenoxyphenyl)pyrene to 90 of CBP.

When voltage was applied between the ITO as a positive electrode and the Al—Li as a negative electrode of the organic EL element, blue light emission was observed at a voltage not less than 4 V. Blue light emission having a luminescence intensity of 5,010 cd/m$^2$ was observed at an applied voltage of 10 V.

EXAMPLE 7

An organic EL element was manufactured as in EXAMPLE 4, except that a 1,3,6,8-tetrakis[3-(3-methyldiphenylamino)phenyl]pyrene layer was used instead of a 1,3,6,8-tetra(4-phenoxyphenyl)pyrene layer as an organic light emitting layer.

When voltage was applied between the ITO as a positive electrode and the Al—Li as a negative electrode of the organic EL element, blue light emission was observed at a voltage not less than 4 V. Blue light emission having a luminescence intensity of 4,120 cd/m$^2$ was observed at an applied voltage of 10 V.

EXAMPLE 8

An organic EL element was manufactured as in EXAMPLE 7, except that a layer that was obtained by concomitant vapor deposition of 1,3,6,8-tetrakis[3-(3-methyldiphenylamino)phenyl]pyrene and BAlq was used instead of a 1,3,6,8-tetrakis[3-(3-methyldiphenylamino)phenyl]pyrene layer as an organic light emitting layer. The BAlq acted as a host. It is considered that the layer was an organic light emitting and electron transporting layer. The weight-based ratio of vapor deposition rates was set to 10 of 1,3,6,8-tetrakis[3-(3-methyldiphenylamino)phenyl]pyrene to 90 of BAlq.

When voltage was applied between the ITO as a positive electrode and the Al—Li as a negative electrode of the organic EL element, blue light emission was observed at a voltage not less than 4 V. Blue light emission having a luminescence intensity of 5,420 cd/m$^2$ was observed at an applied voltage of 10 V.

EXAMPLE 9

An organic EL element was manufactured as in EXAMPLE 4, except that a 1,3,6,8-tetrakis[3,5-bis(3-methyldiphenylamino)phenyl]pyrene layer was used instead of a 1,3,6,8-tetra(4-phenoxyphenyl)pyrene layer as an organic light emitting layer.

When voltage was applied between the ITO as a positive electrode and the Al—Li as a negative electrode of the organic EL element, blue light emission was observed at a voltage not less than 4 V. Blue light emission having a luminescence intensity of 4,180 cd/m$^2$ was observed at an applied voltage of 10 V.

EXAMPLE 10

An organic EL element was manufactured as in EXAMPLE 9, except that a layer that was obtained by concomitant vapor deposition of 1,3,6,8-tetrakis[3,5-bis(3-methyldiphenylamino)phenyl]pyrene and BAlq was used instead of a 1,3,6,8-tetrakis[3,5-bis(3-methyldiphenylamino)phenyl]pyrene layer as an organic light emitting layer. The BAlq acted as a host in this case. The weight-based ratio of vapor deposition rates was set to 10 of 1,3,6,8-tetrakis[3,5-bis(3-methyldiphenylamino)phenyl]pyrene to 90 of BAlq.

When voltage was applied between the ITO as a positive electrode and the Al—Li as a negative electrode of the organic EL element, blue light emission was observed at a voltage not less than 4 V. Blue light emission having a luminescence intensity of 5,600 cd/m$^2$ was observed at an applied voltage of 10 V.

EXAMPLE 11

An organic EL element was manufactured as in EXAMPLE 9, except that a layer that was obtained by concomitant vapor deposition of 1,3,6,8-tetrakis[3,5-bis(3-methyldiphenylamino)phenyl]pyrene and 1,3,6,8-tetrakis(diphenylamino)pyrene was used instead of a 1,3,6,8-tetrakis[3,5-bis(3-methyldiphenylamino)phenyl]pyrene layer as an organic light emitting layer. It is considered that the 1,3,6,8-tetrakis[3,5-bis(3-methyldiphenylamino)phenyl]pyrene was a host, and the 1,3,6,8-tetrakis(diphenylamino)pyrene was a guest. The weight-based ratio of vapor deposition rates was set to 90 of 1,3,6,8-tetrakis[3,5-bis(3-methyldiphenylamino)phenyl]pyrene to 10 of 1,3,6,8-tetrakis(diphenylamino)pyrene.

When voltage was applied between the ITO as a positive electrode and the Al—Li as a negative electrode of the organic EL element, blue light emission was observed at a voltage not less than 4 V. Green light emission having a luminescence intensity of 8,900 cd/m$^2$ was observed at an applied voltage of 10 V.

EXAMPLE 12

The EL element manufactured in EXAMPLE 6 was subjected to continuous operation at a constant current from an initial luminescence intensity of 150 cd/m². The time in which the initial luminescence intensity was decreased to half (half-life in luminescence intensity) was 600 hours.

EXAMPLE 13

The EL element manufactured in EXAMPLE 8 was subjected to continuous operation at a constant current from an initial luminescence intensity of 150 cd/m². The time in which the initial luminescence intensity was decreased to half (half-life in luminescence intensity) was 670 hours.

EXAMPLE 14

The EL element manufactured in EXAMPLE 10 was subjected to continuous operation at a constant current from an initial luminescence intensity of 150 cd/m². The time in which the initial luminescence intensity was decreased to half (half-life in luminescence intensity) was 640 hours.

EXAMPLE 15

The EL element manufactured in EXAMPLE 11 was subjected to continuous operation at a constant current from an initial luminescence intensity of 150 cd/m². The time in which the initial luminescence intensity was decreased to half (half-life in luminescence intensity) was 1,040 hours.

COMPARATIVE EXAMPLE 1

An organic EL element was manufactured as in EXAMPLE 4, except that 1,3,6,8-tetraphenylpyrene was used instead of 1,3,6,8-tetra(4-phenoxyphenyl)pyrene contained in the organic light emitting layer.

When voltage was applied between the ITO as a positive electrode and the Al—Li as a negative electrode of the organic EL element, blue light emission was observed at a voltage not less than 5 V. Blue light emission having a luminescence intensity of 680 cd/m² was observed at an applied voltage of 10 V.

COMPARATIVE EXAMPLE 2

The EL element manufactured in COMPARATIVE EXAMPLE 1 was subjected to continuous operation at a constant current from an initial luminescence intensity of 150 cd/m². The time in which the initial luminescence intensity was decreased to half (half-life in luminescence intensity) was 30 hours.

From these results, it is understood that a 1,3,6,8-tetrasubstituted pyrene compound according to the present invention is an organic light-emitting layer forming material that emits blue light with a high color purity, has a high luminous efficiency, and is stable for a long duration of operation, when used singly or as a guest, and an organic EL element according to the present invention has a high luminous efficiency and a long operation lifetime.

Thus, an organic light-emitting layer forming material that emits blue light with a high color purity, has a high luminous efficiency, and is stable for a long duration of operation, when used singly or as a guest, an organic EL element having a high luminous efficiency and a long operation lifetime, and a high-performance organic EL display having a high luminous efficiency and a long operation lifetime, are provided.

What is claimed is:

1. A 1,3,6,8-tetrasubstituted pyrene compound represented by the following formula (1),

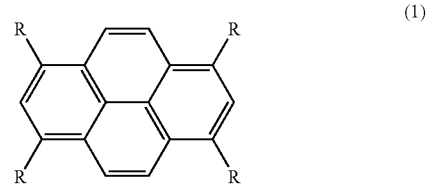

in formula (1), R's have, independently from each other, a structure represented by the following formula (2),

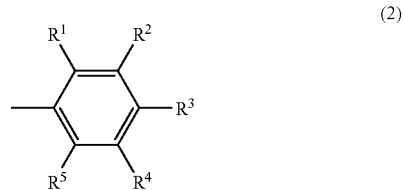

in formula (2), $R^1$-$R^5$ are, independently from each other, hydrogen, a straight-chain or branched-chain aliphatic group, an aromatic group, an alicyclic group, or one of the groups represented by the following formulae (3)-(6),

in formulae (3) to (6), $R^6$-$R^{12}$ are, independently from each other, hydrogen, a straight-chain or branched-chain aliphatic group, an aromatic group, or an alicyclic group and at least one of $R^1$-$R^5$ is represented by formulae (3) and $R^6$ and $R^7$ in formula (3) are, independently from each other, an aromatic group or at least one of $R^1$-$R^5$ is represented by formula (6) and $R^{12}$ in said formula (6) is an aromatic group.

2. A 1,3,6,8-tetrasubstituted pyrene compound according to claim 1, wherein at least one of $R^1$-$R^5$ is represented by formula (3) and $R^6$ and $R^7$ in said formula (3) are, independently from each other, an aromatic group.

3. A 1,3,6,8-tetrasubstituted pyrene compound according to claim 1, wherein at least one of $R^1$-$R^5$ is represented by formula (6) and $R^{12}$ in said formula (6) is an aromatic group.

4. A 1,3,6,8-tetrasubstituted pyrene compound according to claim 1 that is used as an organic light-emitting layer forming material in an organic electroluminescence element.

5. A 1,3,6,8-tetrasubstituted pyrene compound according to claim 1 that is used as an organic light-emitting layer forming material in the capacity of a host or a guest in an organic electroluminescence element.

6. An organic electroluminescence element having an organic light-emitting layer between a positive electrode and a negative electrode, wherein said organic light-emitting layer contains a 1,3,6,8-tetrasubstituted pyrene compound represented by the following formula (1) as an organic light-emitting layer forming material,

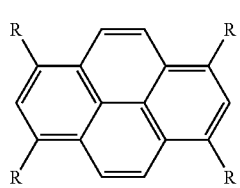

(1)

in formula (1), R's have, independently from each other, a structure represented by the following formula (2),

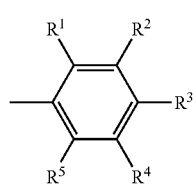

(2)

in formula (2), $R^1$-$R^5$ are, independently from each other, hydrogen, a straight-chain or branched-chain aliphatic group, an aromatic group, an alicyclic group, or one of the groups represented by the following formulae (3)-(6),

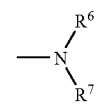

(3)

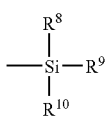

(4)

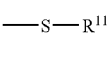

(5)

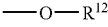

(6)

in formulae (3) to (6), $R^6$-$R^{12}$ are, independently from each other, hydrogen, straight-chain or branched-chain aliphatic group, an aromatic group, or an alicyclic group and
at least one of $R^1$-$R^5$ is represented by formulae (3) and $R^6$ and $R^7$ in formula (3) are, independently from each other, an aromatic group
or
at least one of $R^1$-$R^5$ is represented by formula (6) and $R^{12}$ in said formula (6) is an aromatic group.

7. An organic electroluminescence element according to claim 6, wherein said 1,3,6,8-tetrasubstituted pyrene compound represented by formula (1) is an organic light-emitting layer forming material in the capacity of a host or a guest.

8. An organic electroluminescence element according to claim 6, wherein said organic light-emitting layer is a single layer of a 1,3,6,8-tetrasubstituted pyrene compound represented by said formula (1).

9. An organic electroluminescence element according to claim 6, wherein at least one of $R^1$-$R^5$ is represented by formula (3) and $R^6$ and $R^7$ in said formula (3) are, independently from each other, an aromatic group.

10. An organic electroluminescence element according to claim 6, wherein at least one of $R^1$-$R^5$ is represented by formula (6) and $R^{12}$ in said formula (6) is an aromatic group.

11. An organic electroluminescence element according to claim 6, wherein said organic light-emitting layer contains one or more aromatic amine compounds represented by the following formula (7),

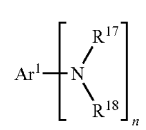

(7)

in formula (7), $Ar^1$ is a di, tri or tetravalent aromatic group that may have a substituent group; $R^{17}$ and $R^{18}$ are, independently from each other, a monovalent aromatic group; and n is an integer of 2-4.

12. An organic electroluminescence element according to claim 11, wherein the aromatic amine compound represented by formula (7) is N,N'-dinaphthyl -N,N'-diphenyl-[1,1'-biphenyl]-4,4'-diamine represented by the following formula (8)

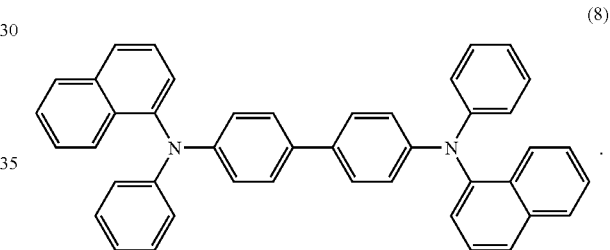

(8)

13. An organic electroluminescence element according to claim 6, wherein said organic light-emitting layer contains one of more carbazole compounds represented by the following formula (9),

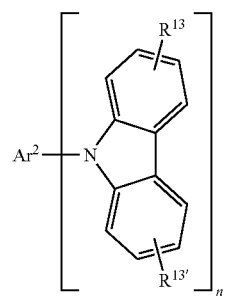

(9)

in formula (9), $Ar^2$ is a di, tri or tetravalent aromatic group that may have a substituent group; $R^{13}$ and $R^{13'}$ are, independently from each other, a hydrogen atom, a halogen atom, or an alkyl, aralkyl, alkenyl, aromatic, cyano, amino, acyl, alkoxycarbonyl, carboxy, alkoxy, alkylsulfonyl, hydroxyl, amide or aromatic oxy group ; and n is an integer of 2-4.

14. An organic electroluminescence element according to claim 13, wherein the carbazole compound represented by formula (9) is 4,4'-bis(9-carbazolyl)-biphenyl represented by the following formula (10)

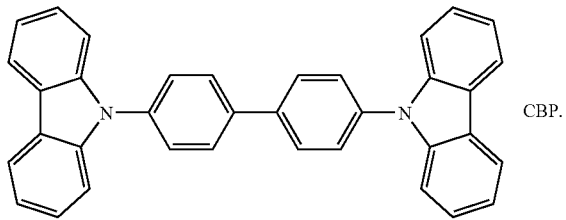

CBP.

15. An organic electroluminescence element according to claim 6, wherein said organic light-emitting layer contains one or more hydroxyquinoline-oxyaryl complex represented by the following formula (11),

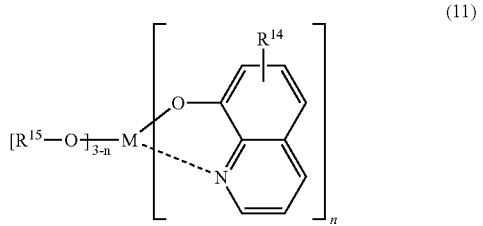

in formula (11), $R^{14}$ is hydrogen or an alkyl group that may have a substituent group; $R^{15}$ is an aromatic group; M is a trivalent metal; and n is 1 or 2.

16. An organic electroluminescence element according to claim 15, wherein the hydroxyquinoline-oxyaryl complex represented by formula (11) is an aluminum hydroxyquinoline-oxybiphenyl complex represented by the following formula (12)

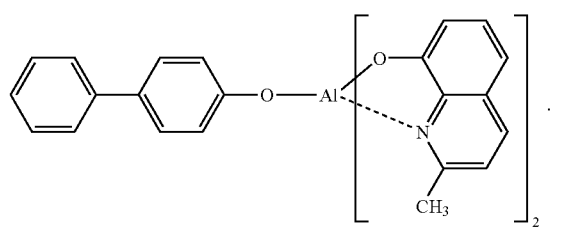

\* \* \* \* \*